United States Patent
Stantchev

(10) Patent No.: US 11,299,471 B2
(45) Date of Patent: Apr. 12, 2022

(54) APPARATUS AND METHOD FOR REMOVING A COMPONENT FROM A SOLUTION

(71) Applicant: George Stantchev, Phoenix, AZ (US)

(72) Inventor: George Stantchev, Phoenix, AZ (US)

( * ) Notice: Subject to any disclaimer, the term of this patent is extended or adjusted under 35 U.S.C. 154(b) by 0 days.

(21) Appl. No.: 16/661,308

(22) Filed: Oct. 23, 2019

(65) Prior Publication Data

US 2020/0131146 A1 Apr. 30, 2020

Related U.S. Application Data

(60) Provisional application No. 62/750,133, filed on Oct. 24, 2018.

(51) Int. Cl.
*C07D 311/80* (2006.01)
*B01D 11/04* (2006.01)
*B01D 1/00* (2006.01)
*B01D 1/14* (2006.01)

(52) U.S. Cl.
CPC ........ *C07D 311/80* (2013.01); *B01D 11/0465* (2013.01); *B01D 11/0469* (2013.01)

(58) Field of Classification Search
CPC .............. C07D 311/80; B01D 11/0465; B01D 11/0469; B01D 1/14; B01D 1/0082
See application file for complete search history.

(56) References Cited

U.S. PATENT DOCUMENTS

| 5,173,318 A | * | 12/1992 | Leu | C12H 1/12 426/238 |
| 2011/0070330 A1 | * | 3/2011 | Watson | C12G 3/07 426/11 |
| 2016/0038437 A1 | * | 2/2016 | Whittle | A61K 31/05 514/733 |

OTHER PUBLICATIONS

Benitez, F. J., "Degradation of carbofuran by using ozone, UV radiation and advanced oxidation processes." Journal of hazardous materials 89.1 (2002): 51-65.*
Kim, J-G., "Application of ozone for enhancing the microbiological safety and quality of foods: a review." Journal of food protection 62.9 (1999): 1071-1087.*

* cited by examiner

*Primary Examiner* — John M Mauro
(74) *Attorney, Agent, or Firm* — Rosenberg, Klein & Lee

(57) ABSTRACT

An apparatus and method for removing a compound from a solution are disclosed. The apparatus includes a vessel, a solution heater, and an aeration device, wherein the solution heater and the aeration device are connected to the vessel. The solution is contained in the vessel and heated by the solution heater. The aeration device provides aeration to the heated solution for agitating the heated solution, and the component is thereby removed from the solution.

28 Claims, 7 Drawing Sheets

APPARATUS AND METHOD FOR REMOVING A COMPONENT FROM A SOLUTION

REFERENCE TO RELATED APPLICATIONS

This non-provisional application claims priority under 35 U.S.C. § 119(e) to U.S. Provisional Patent Application No. 62/750,133, filed Oct. 24, 2018, the entire contents of which are incorporated herein by reference.

TECHNICAL FIELD

The present disclosure relates to an apparatus and a method for removing or degrading which can be commonly called remediation of a component from a plant or a solution, further for simplification all will be referenced as solution as the solution may reside in plants and other forms of delivery, more particularly, to an apparatus and a method that removes a component from a solution by applying external influence and aeration to the solution.

BACKGROUND

Cannabis plants may contain or produce up to hundreds of compounds, some of which are active ingredients that affect people mentally or/and physically, known as cannabinoids. The well-known cannabinoids include tetrahydrocannabinol (THC), cannabidiol (CBD), cannabigerol (CBG), cannabichromene (CBC), and cannabinol (CBN), and these cannabinoids have been proven to have medical benefits in different areas. Thus, there have been many researches on how to precisely extract or isolate either desirable or undesirable compounds from plant extracts to obtain a specific component content.

It has been known that cannabigerolic acid (CBGA) is a chemical component in cannabis plants and the plant produces enzymes that convert CBGA into various cannabinoids, which are precursors of the cannabinoids mentioned above. One such cannabinoid is tetrahydrocannabinol carboxylic acid (THCA), and the decarboxylation of THCA is usually through heat and converts THCA into THC. THCA also converts to CBNA when it loses hydrogen molecules and oxidizes. The latter process (THCA to CBNA) occurs through prolonged exposure to air. Like THCA becoming THC, decarboxylation converts CBNA to CBN.

Currently, to qualify as a hemp plant or its products, THC level contained therein must be less than 0.3%, and as of the state of the science, there are 3 possible ways which THC degrades: degradation, oxidation, and enzymatic. However, a heat of over 180° C. or long time storage degrades the THC and the amount of heat will damage the quality of the extract by oxidizing the existing CBD as well as evaporating good portion of the extract, thereby lowering and thickening the consistency.

SUMMARY

An object of the present disclosure is to provide an improved solvent-less process for removing THC from hemp plants and extracts utilizing accelerated natural conversion of the cannabinoids. The process essentially applies external influence and aeration to the plant and/or extract in order to convert THC to other cannabinoids without loss to the CBD in the extract volume. The above process is performed under minimal temperature conditions to isolate one or more components in-process and keep the full spectrum components unharmed by the heat.

Therefore, it is an object of the present disclosure to provide an apparatus for removing a component from a solution. The apparatus includes a vessel for containing the solution, a solution heater connected to or in contact with the vessel for heating the solution, and an aeration device connected to the vessel for providing aeration to the heated solution. The heated solution is agitated by the aeration and the component is thereby removed or converted from the solution.

In one embodiment of the present disclosure, the aeration device includes at least one aeration pipe disposed in the vessel.

In one embodiment of the present disclosure, the aeration device also includes a gas source in fluid connection to the at least one aeration pipe for providing a gas.

In one embodiment of the present disclosure, the gas source is a gas tank or a gas generator.

In one embodiment of the present disclosure, the gas is compressed gas, a combined gas mixture of non-naturally occurring gas, oxygen, nitrogen, air, argon, or any combination thereof.

In one embodiment of the present disclosure, the aeration device further includes a gas heater and a temperature sensor. The gas heater is disposed between the gas source and the at least one aeration pipe for heating the gas before introducing the gas into the at least one aeration pipe. The temperature sensor is disposed between the gas heater and the at least one aeration pipe for controlling a temperature of the heated gas.

In one embodiment of the present disclosure, a temperature of the heated gas is higher than a temperature of the heated solution.

In one embodiment of the present disclosure, the apparatus further includes a lid disposed over the vessel.

In one embodiment of the present disclosure, the aeration of the heated solution includes an addition of an oxidizing agent.

In one embodiment of the present disclosure, the oxidizing agent is ozone and the apparatus further includes an ozone generator connected to the aeration device.

In one embodiment of the present disclosure, the apparatus further includes a radiation device disposed close to the vessel for irradiating the heated solution. The radiation device includes an electromagnetic spectrum source.

In one embodiment of the present disclosure, the electromagnetic spectrum source is an IR lamp and the radiation device further includes a filter disposed between the electromagnetic spectrum source and the heated solution for limiting a radiation exposure to narrow the spectrum to a desired spectrum.

In one embodiment of the present disclosure, the IR lamp is an IR lamp with a wide spectrum radiation range, and the desired spectrum is in a range of 2-25 micrometers.

In one embodiment of the present disclosure, the electromagnetic spectrum source is a coil or an antenna focusing EMI energy to the heated solution.

It is another object of the present disclosure to provide a method for removing or converting a component from a solution. The method includes the steps of disposing the solution in a vessel, heating the solution with a solution heater, and aerating the heated solution by an aeration device to agitate the heated solution until the component is removed/converted from the solution.

In one embodiment of the present disclosure, the aeration device includes at least one aeration pipe disposed in the vessel, a gas source in fluid connection with the at least one aeration pipe, and a gas heater disposed between the at least one aeration pipe and the gas source. The step of aerating the heated solution includes providing a gas from the gas source, heating the gas with the gas heater, and introducing the heated gas into the heated solution via the at least one aeration pipe.

In one embodiment of the present disclosure, the method further includes applying an external influence to the heated solution.

In one embodiment of the present disclosure, the step of applying the external influence is heating the gas to a temperature higher than the heated solution, adding an oxidizing agent to the heated gas, or irradiating the heated solution by a radiation device.

In one embodiment of the present disclosure, the oxidizing agent is ozone, and the radiation device includes an electromagnetic spectrum source disposed close to the vessel and a filter disposed between the electromagnetic spectrum source and the heated solution, wherein the electromagnetic spectrum source is an IR lamp and the filter limits a radiation exposure to a desired spectrum.

In one embodiment of the present disclosure, the IR lamp is an IR lamp with a wide spectrum radiation range, and the desired spectrum is in a range of 2-25 micrometers.

In one embodiment of the present disclosure, before disposing the solution, the method further includes a preparation process. The preparation process includes the steps of: providing a starting material, performing an HPLC/GC chromatography analysis on the starting material, removing volatile compounds from the starting material to form the solution, performing calculation for behavior of the component and the solution in the vessel, and programing parameters of the vessel, the solution heater, and the aeration device.

In one embodiment of the present disclosure, after the component is removed or converted from the solution, a second HPLC chromatography analysis is performed. If a result of the analysis meets a defined standard, the volatile compounds are re-introduced to the solution. If the result does not meet the defined standard, the preparation process is repeated, wherein the solution without the component therein servers as the starting material in the repeated process.

In one embodiment of the present disclosure, the solution is hemp extract, the component is tetrahydrocannabinol (THC), the starting material is a full spectrum oil, and the volatile compounds are terpenes.

BRIEF DESCRIPTION OF THE DRAWINGS

The structure as well as preferred modes of use, further objects, and advantages of this present disclosure will be best understood by referring to the following detailed description of some illustrative embodiments in conjunction with the accompanying drawings, in which.

DETAILED DESCRIPTION OF THE PREFERRED EMBODIMENTS

Figure 1:
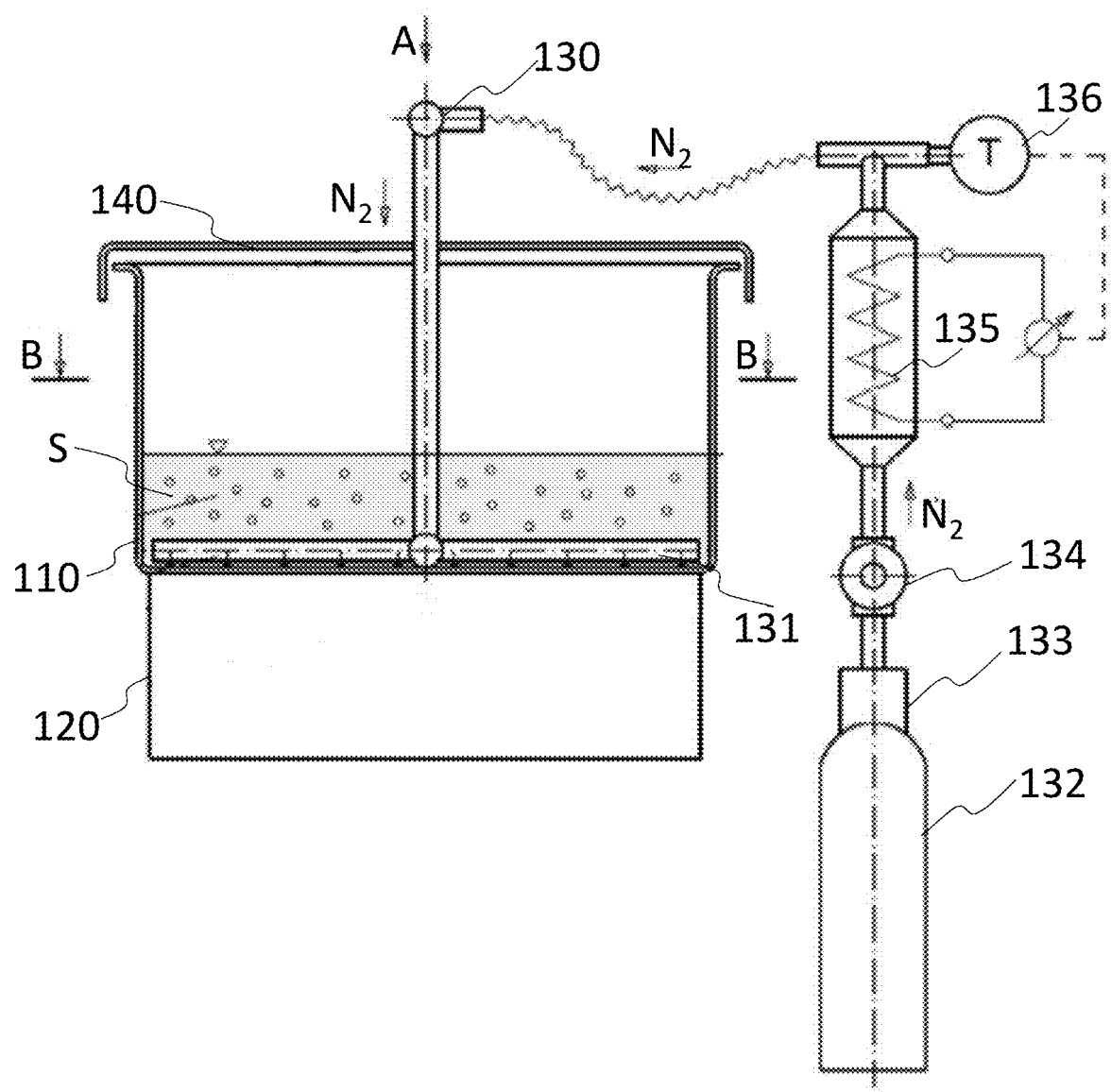
FIG. 1 is a schematic diagram of an apparatus for removing a component from a solution according to a first embodiment of the present disclosure.

FIG. 1 is a schematic diagram of an apparatus for removing a component from a solution according to a first embodiment of the present disclosure. The first embodiment removes and/or converts a component from a solution by degradation. The apparatus 10 includes a vessel 110, a solution heater 120, and an aeration device 130. The vessel 110 contains a solution S therein. The vessel 110 is preferably a degassing pot but the present disclosure is not limited thereby. The solution heater 120 is connected to or in contact with the vessel for heating the solution S, wherein the solution heater 120 is preferably a regulated electric heater. The aeration device 130 is connected to the vessel 110 for providing aeration to the heated solution S, and the aeration device 130 includes at least one aeration pipe 131 disposed in the vessel 110 to introduce airflow or gas into the heated solution S. The solution S is agitated by the aeration and thereby converting and/or removing the component from the solution S.

Figure 2:
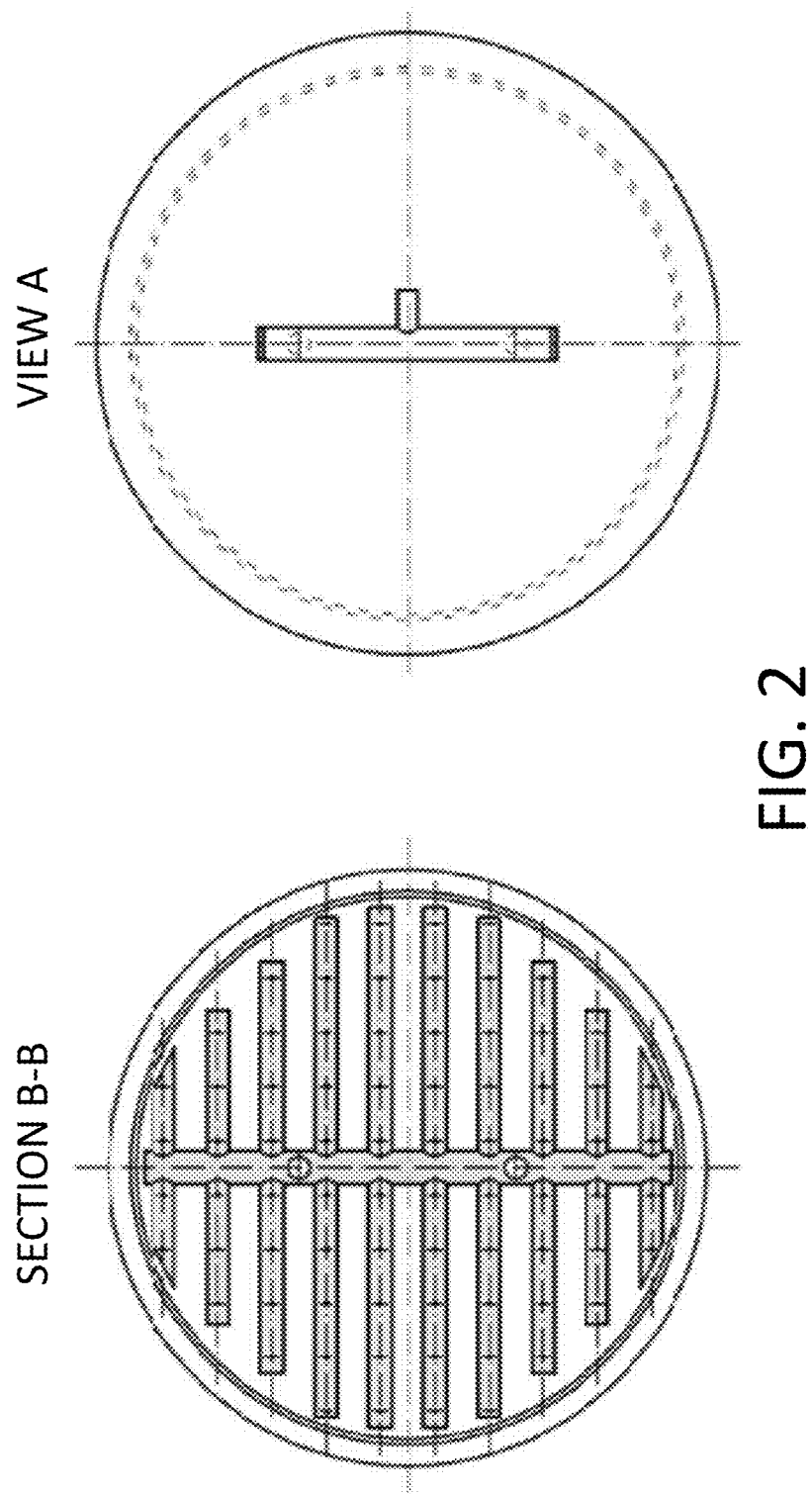
FIG. 2 illustrates a top view and a sectional view of aeration pipes of an aeration device according to an embodiment of the present disclosure.

Referring to FIG. 2, which illustrates a sectional view along line B-B in FIG. 1 and a top view from point A in FIG. 1, the at least one aeration pipe 131 may form a net of aeration pipes and be disposed at the bottom of the vessel 110, and the aeration pipe 131 may also extend outside of the vessel 110 and connect to a gas source 132, wherein the gas source 132 is a gas tank or a gas generator with pump, and preferably a pressurized air tank. In other words, the aeration device 130 further includes a gas source 132 for providing a gas and is in fluid connection with the aeration pipe 131. In the apparatus of the present disclosure, the solution S is agitated by aerating with a gas, like air or oxygen, to speed up the natural transformation. In order to control the conversion, an inert gas such as nitrogen and/or argon can be used in the mixture to aerate the apparatus. Moreover, any other non-naturally occurring gas mixture or compressed gas may be used to improve the process.

The aeration device 130 further includes a pressure reducing unit 133, a regulation valve 134, a gas heater 135, and a temperature sensor 136. The pressure reducing unit 133 is connected to the gas source 132 for controlling the pressure of the gas coming out of the gas source 132. The regulation valve 134 is connected to the pressure reducing unit 133 for controlling the gas flow from the gas source 132. The gas heater 135 is connected to the regulation valve 134 for heating the gas and the temperature sensor 136 connected to the gas heater 135 is used to control a temperature of the heated gas. More specifically, the gas heater 135 is disposed between the gas source 132 and the aeration pipe 131 for heating the gas before introducing the gas into the aeration pipe 131.

The apparatus 10 further includes a lid 140 disposed over the vessel 110 for preserving the environment unified and sterile inside the vessel 110.

When using the apparatus 10 to convert and/or remove a component like THC from a solution S like hemp extract, the hemp extract containing THC is put in the vessel 110 and heated to 40~90° C. by the solution heater 120 to be maintained in liquid state. The air coming from the gas source 132, which is an air tank in this example, may be an inert gas such as nitrogen or argon to prevent the solution S from unintentional oxidation and color change. That gas may also be supplied from a natural nitrogen generator via a pump (not shown) instead. The gas from the tank passes through the regulation valve 134 and is preheated to 145-200° C. by the gas heater 135. The temperature of the gas is regulated by a thermal regulator (not shown) connected to the temperature sensor 136. By using the nitrogen gas at 145-200° C. to aerate the hemp extract in liquid-state at 40~90° C., where the temperature of the heated gas is higher than the temperature of the heated solution, the hemp extract is agitated and the natural transformation of THC is sped up, and hence THC is converted and thus removed from the hemp extract.

Figure 3:
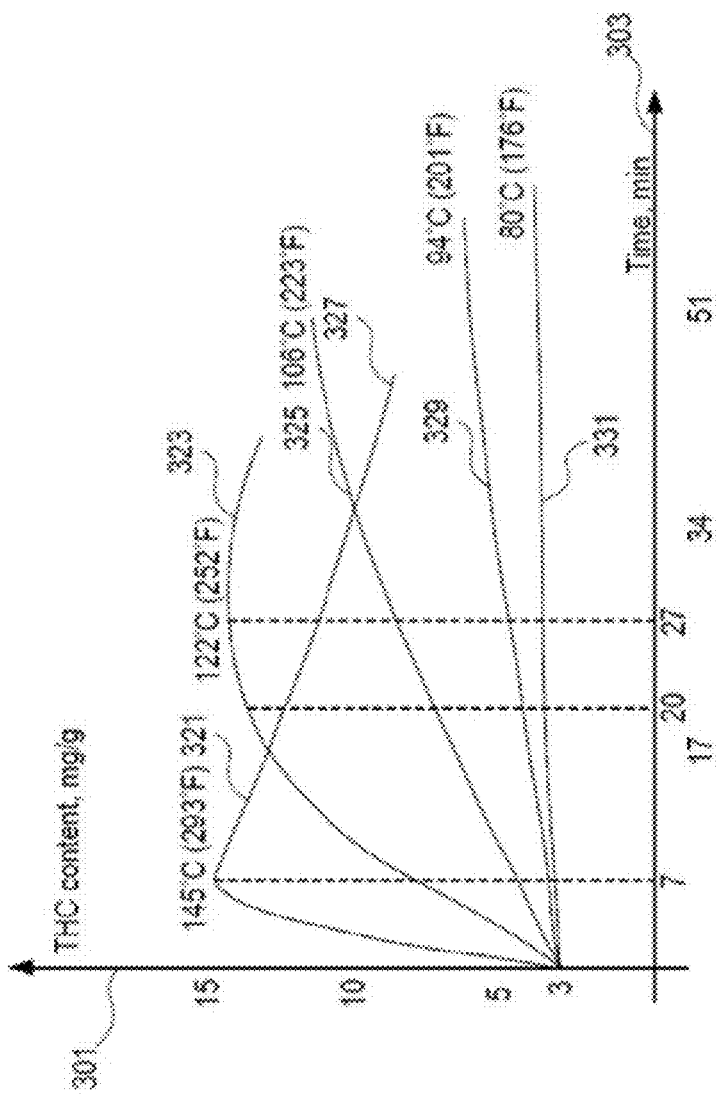
FIG. 3 is a schematic conversion chart for THC degradation.

FIG. 3 shows the various curves for THC degradation. It can be seen that with 122° C. air stream, the degradation will start after 30 min of gas exposure, and for airstream at 145° C., the gas exposure only required 7 minutes. Although it will take, for example, around 3~5 hours of exposure to intense heat for full THC degradation, but heated air stream can speed up the degradation process. It is to be noted that the degradation time is specific to how many percent of THC is in the starting THC material and what the wax and lipid consistency of the starting extract are.

Figure 4:
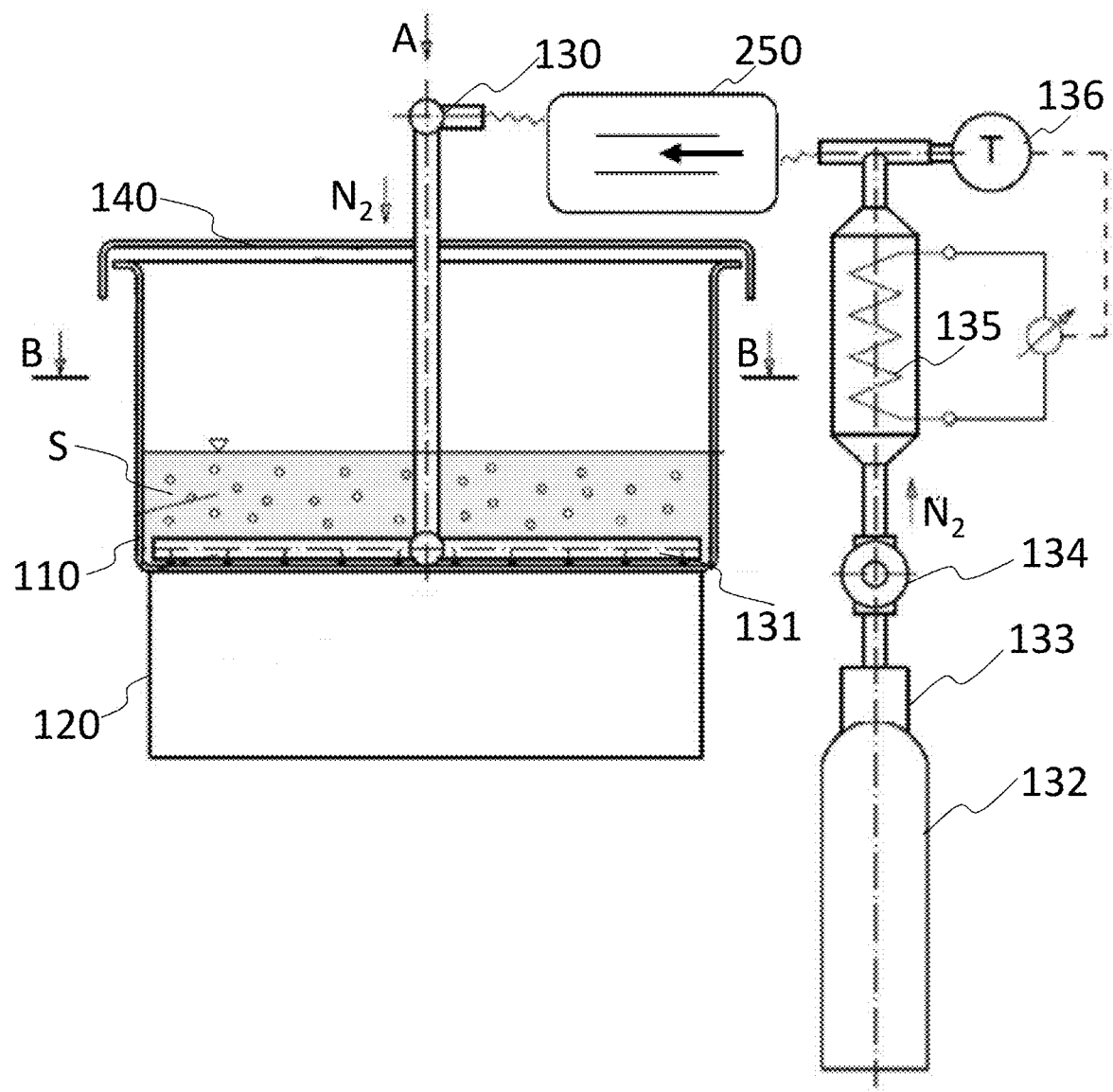
FIG. 4 is a schematic diagram of an apparatus for removing a component from a solution according to a second embodiment of the present disclosure.

FIG. 4 is a schematic diagram of an apparatus for removing a component from a solution according to a second embodiment of the present disclosure. The second embodiment converts/removes a component from a solution by oxidation. The apparatus 20 of the second embodiment is similar to the apparatus 10 of the first embodiment, and the difference is that the apparatus 20 includes an ozone generator 250 connected to the aeration device 130, wherein the ozone generator 250 adds an oxidizing agent to the gas for the aeration of the heated solution S. The remaining elements in the apparatus 20 are similar to those in the apparatus 10 and are not described again herein.

Unlike the apparatus 10 where the removal/conversion of component from the solution S is performed under heat, the oxidation of the apparatus 20 is performed by utilizing oxidizing agent, for example, ozone. Since ozone is not a very stable mixture and because of its' short half-life, it needs to be generated immediately before application. The two main principles of ozone generation are UV-light and corona-discharge, wherein the latter is the most effective way of generating ozone.

For the production of ozone, ambient air supplied by a compressor can be used, or pure oxygen supplied by an oxygen generator, or sometimes by oxygen bottles can also be used. To condition this air, air dryers and dust filters are used which are known art and will not be a subject in the present disclosure. To break down the remaining ozone after use, ozone destructors are applied. The mechanism of an ozone destructor can be based on different principles. Usually a catalyst is applied, which accelerates the decomposition of ozone into oxygen, and the catalysis is for example, magnesium oxide.

When using the apparatus 20 to convert/remove a component like THC from a solution S like cannabis-derived extract, the extract is put in the vessel 110, or in this example, a degassing pot. The extract is heated by the solution heater 120, or a regulated heater, to 40~90° C., in order to maintain a necessary liquidity for the aeration to occur. There are at least one aeration pipe 131 disposed on the bottom of the vessel 110 and connected to a gas source 132 with the pressure reducing unit 133 and the gas heater 135. The gas source 132 is a pressurized gas vessel equipped with pressure regulator and heating component. The gas heater 135 preheats the gas entering the aerating pipe 131 to the same temperature as the degassing pot, which is 40~90° C., wherein the temperature is controlled by precise thermostat like the temperature sensor 136. In other embodiments, the gas source 132/pressurized gas vessel can be substituted by air compressor and the gas temperature can be controlled by reading the temperature with the temperature sensor 136 and regulating the gas heater 135/heating element.

The lid 140 on the top of the vessel 110 allows the aeration pipe to exit and connect to the gas heater 135/regulated heater where the temperature sensor 136 is installed. The ozone generator 250 is installed or disposed in between the gas heater 135 and the aeration pipe 131, wherein the ozone generator 250 is, for example, an ozonating circuit. The flow rate of the gas matches the ozonation intensity, for example, 10 g/h ozonator will be sufficient to provide more than 20% ozonation of oxygen in the airstream.

By adding oxidizing agent to the gas that aerates the extract at the same temperature, THC is removed quickly via oxidation and the extract loses its odor completely. If ozone is used for an oxidation of a 1 kg extract with the apparatus 20 of the present disclosure, the removal takes approximately 1 hour. The speed for removal depends on the ozonation level, amount of the THC in the extract, and amount of the wax and lipid content.

Figure 5:
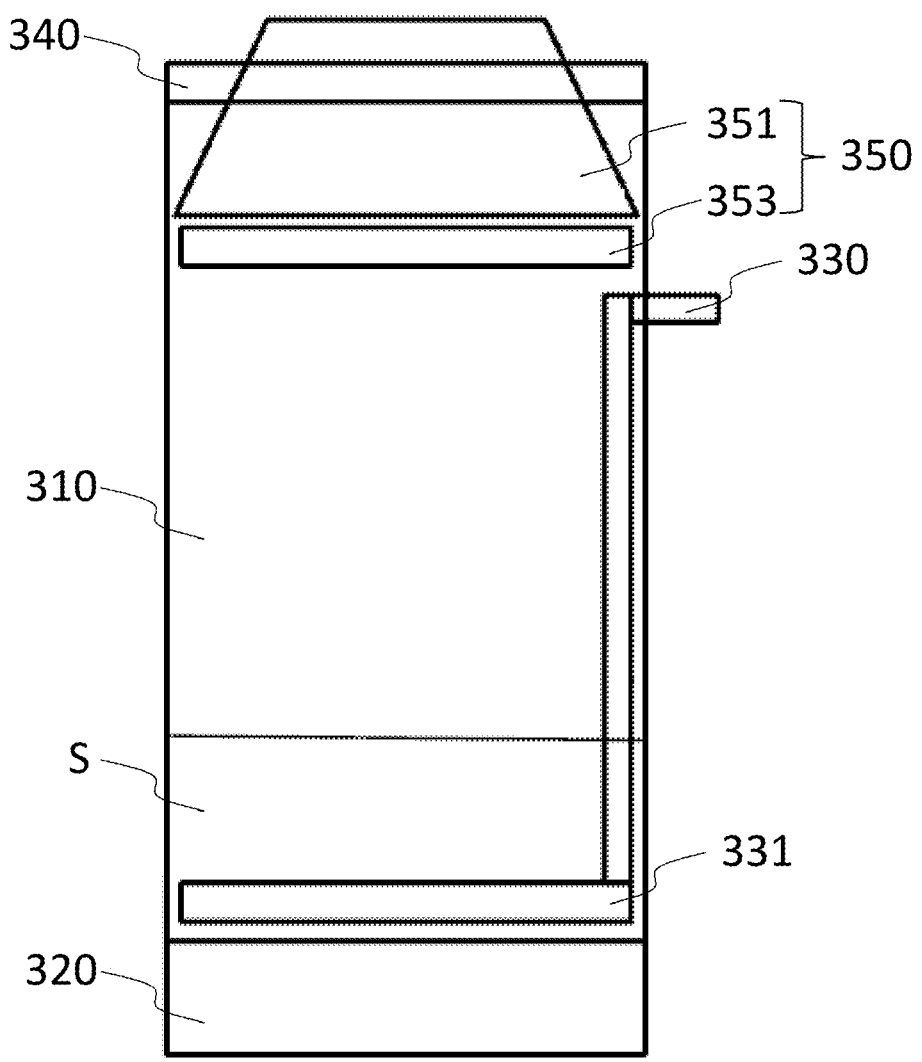
FIG. 5 is a schematic diagram of an apparatus for removing a component from a solution according to a third embodiment of the present disclosure.

FIG. 5 is a schematic diagram of an apparatus for removing a component from a solution according to a third embodiment of the present disclosure. The third embodiment removes/converts a component from a solution by enzymatic conversion utilizing a portion of the solar light spectra beneficial for such conversion. As known to one familiar with the art the electromagnetic spectrum is extending from the radio waves through microwave, infrared, visible light, x-rays and gamma rays. In this present disclosure we will use the terminology of electromagnetic spectrum for wide wavelength sources in that region. The apparatus 30 of the third embodiment is similar to the apparatus 20 of the second embodiment, wherein the apparatus 30 also includes a vessel 310, a solution heater 320, an aeration device 330, and a lid 340, and the difference is that the apparatus 30 further includes a radiation device 350 and does not include the ozone generator 250. The vessel 310, the solution heater 320, the aeration device 330, and the lid 340 of the apparatus 30 are similar to the vessel 110, the solution heater 120, the aeration device 130, and the lid 140 of the apparatus 10 & 20, and therefore are not described in detail herein.

Referring to FIG. 5, the radiation device 350 includes an electromagnetic spectrum source 351 and a filter 353. As noted above, the electromagnetic spectrum source 351 can be a narrow or wide spectrum wavelength source. The electromagnetic spectrum source 351 is disposed on top of the vessel 310 for irradiating the heated solution and the filter 353 is disposed between the electromagnetic spectrum source 351 and the heated solution for limiting a radiation exposure to a desired spectrum, wherein the desired spectrum is preferably to be in a range of 2-25 micrometers. As shown in FIG. 5, the vessel 350 is covered by the electromagnetic spectrum source 351 followed by the filter 353 to limit the radiation. The filter 353 is implemented in connection with the electromagnetic spectrum source 351. For example, if the electromagnetic spectrum source 351 is an IR source, the filter 353 is set to limit the radiation in the range of 2-25 micrometer. However, the present disclosure does not limit where and how the radiation device, including its components, is disposed. In other embodiments, the radiation device 350 can be disposed close to the vessel as long as the heated solution in the vessel 310 can be irradiated. In other embodiments, the electromagnetic spectrum source 351 is an IR lamp, preferably with a wide spectrum radiation range, or a coil or antenna focusing the EMI energy to the heated solution. It is important to note that if the electromagnetic spectrum source is limited to the correct wavelength by design, the filter may not be necessary.

Take removing THC in cannabis derived extract for example. The extract is placed in the vessel 310 of the apparatus 30, wherein the vessel 310 is a degassing pot. The extract is heated by a solution heater 320 so as to maintain a necessary liquidity for the aeration to occur, wherein the solution heater 320 is a regulated heater. The aeration pipes of the aeration device 330 are disposed on the bottom of the vessel 310 and connected to a gas source (not shown) of the aeration device, wherein the gas source is a pressurized gas vessel equipped with pressure regulator and heating component (not shown). The gas entering the aerating pipes are preheated to the same temperature as the degassing pot, which in this case is 40~90° C.

The pressurized gas vessel can be substituted by an air compressor and the gas temperature can be controlled by reading the temperature with a temperature sensor (not shown) and regulating the heating component. There is a lid 340 disposed on the top of the vessel 310, and the lid 340 connects the vessel 310 with the radiation device 350, more specifically, with the electromagnetic spectrum source 351 of the radiation device 350. The electromagnetic spectrum source 351 is an active EMI radiation component. The active EMI radiation component can radiate a carefully selected set of frequencies to weaken the bonds of the solution components and stimulate enzymatic conversion thereof in natural environment.

The electromagnetic spectrum source 351 can also be an IR lamp that is capable of creating electromagnetic radiation in a wide spectrum radiation range. A spectral range of 2 to 25 micrometers can be best created by introducing a filter 353 on the path of the electromagnetic field that maintains the radiation in range. In the case of THC removal, the infrared sources close to the sunlight spectrum will naturally stimulate the degradation of THC. This radiation activates the enzymes and in collaboration converts the terpene structure and accelerates the degradation of THC. The source of the electromagnetic field may be externally modulated to improve efficiency and the speed of the transformation.

In other words, the embodiment in FIG. 5, shows the extract being located in a degassing pot that is placed on a heating pot heated by a regulated heater and aerated by aeration pipe fixture. The fixture is connected to an aeration/gas source (not shown) as described in previous embodiments. The aeration/gas source may be a compressed air or a generator of airflow, as example, nitrogen generator.

An apparatus built according to the third embodiment of the present disclosure as shown in FIG. 5 utilizing an IR source with a wide spectrum radiation range and a use of a filter limiting the spectrum range within a desired spectrum, like 2 to 25 micrometer, to degrade the THC in a rate of approximately 0.1%/hr. This is approximately 32 hours for full THC removal in hemp extract.

When the electromagnetic spectrum source or an EMI source is set in the 1 to 32 kHz range, the apparatus will proceed with THC degradation at around 0.03%/hr. This will set the complete THC degradation to around 1000 hours. The electromagnetic spectrum source may be adjusted in the 100-150 MHz range and show similar results. The heat from the heater and the air flow does not need to increase 100° C. to maintain the process from occurring. In this implementation the electromagnetic spectrum source may be designed as a coil or antenna focusing the EMI energy to the solution.

Figure 6:
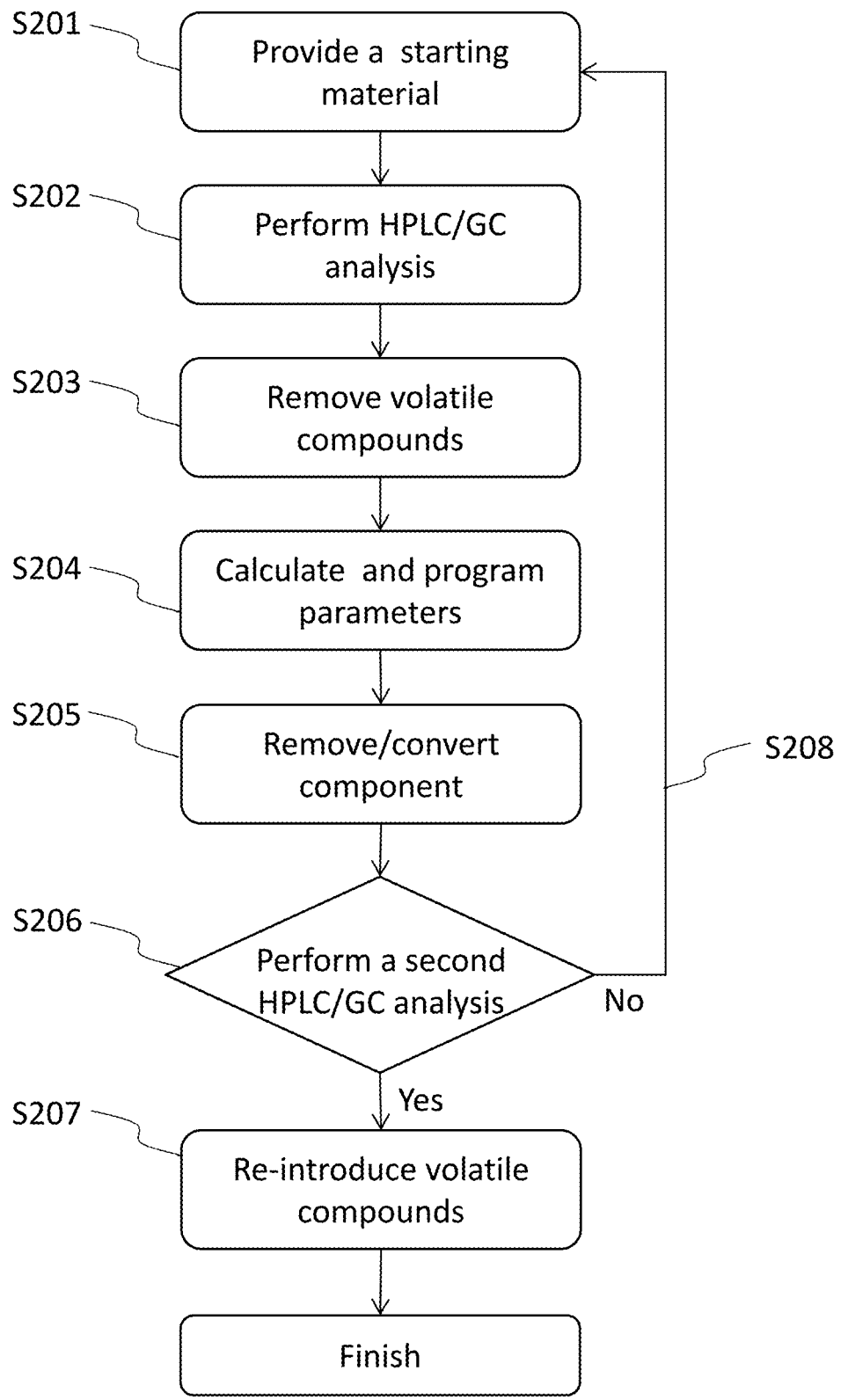
FIG. 6 is a flow chart of a method for removing a component from a solution according to an embodiment of the present disclosure.

FIG. 6 is a flow chart illustrating a method for removing a component from a solution according to an embodiment of the present disclosure, wherein the apparatus utilizes the following method for component conversion/removal and included in the method is a preparation process to prepare the solution for component removal/conversion. First, in step S201, a starting material is provided. In the case of THC removal, a full spectrum oil such as extracted hemp oil, distillate oil, crude oil, complete dry or wet plant, etc. is allocated.

Step S202. Perform a HPLC/GC (high performance liquid chromatography—gas chromatography) chromatographic analysis of the starting material to obtain results showing composition potency, volatile compounds, and their mass concentrations. In the case of THC removal, the starting material is a full spectrum extracted hemp oil, the composition potency is cannabinoid potency, and the volatile compounds are terpenes.

Step S203. Utilize a simple distillation process to remove the volatile compounds as they will be lost in the process and thereby forming the solution for component removal. The most standard distillation is a short path distillation, but it also can be any similar distillation such as wiped film, spinning band, classic or any column chromatography. This step is not necessary for all starting materials.

Step S204. Perform a calculation for the behavior of the component and the solution in the apparatus according to one of the aforementioned embodiments to determine the optimal removal parameters: temperature of the solution heater, air gas consistency, gas flow rate, starting solution, EMI frequency, temperature of the gas heater, and the flow rate of the system/apparatus. The calculated parameters are then programed in the system/apparatus to ensure proper control of the environment for removing the component. Then in step S205, remove or convert the component from the solution. In the case of THC removal, the behavior of the THC is calculated and the THC removal is performed according to the calculated parameters.

S206. Perform a HPLC chromatographic analysis of the solution to determine the effectiveness of the removal by conversion. This is to test whether the component has been successfully removed/converted from the solution or/and whether the presence of the component in the solution meets a defined standard or is below a desired limit. In the case of THC removal in hemp extract, the allowed standard is anywhere between 0.05% to 0.3%.

Based on the test result, if more removal/conversion of the component is needed, proceed to step S208, or else proceed to step S207.

More specifically, if the component remaining in the solution is below the desired limit, for example under 0.3% of THC in hemp extract, then the component removal/conversion is determined to be successful and no component removal is further required. Subsequently, step S207 is performed. However, if the component remaining in the solution is higher than the desired limit, for example more than 0.3% of THC in the hemp extract, then further removal of the component is required, and therefore step S208 is performed.

S206. If needed, re-introduce the volatile compounds to maintain the original parameters of the solution less the component remediated. In the case of THC removal, once the THC level is under the limit of 0.3%, terpenes are re-introduced into the full spectrum extracted hemp oil which now has less or no THC component.

S208. Return to step S201 and repeat the steps thereafter, wherein the solution serves as the starting material in the repeated process. These steps relating to the preparation of the solution and the removal/conversion of component are repeated until the presence of the component in the solution meets the defined standard.

Figure 7:
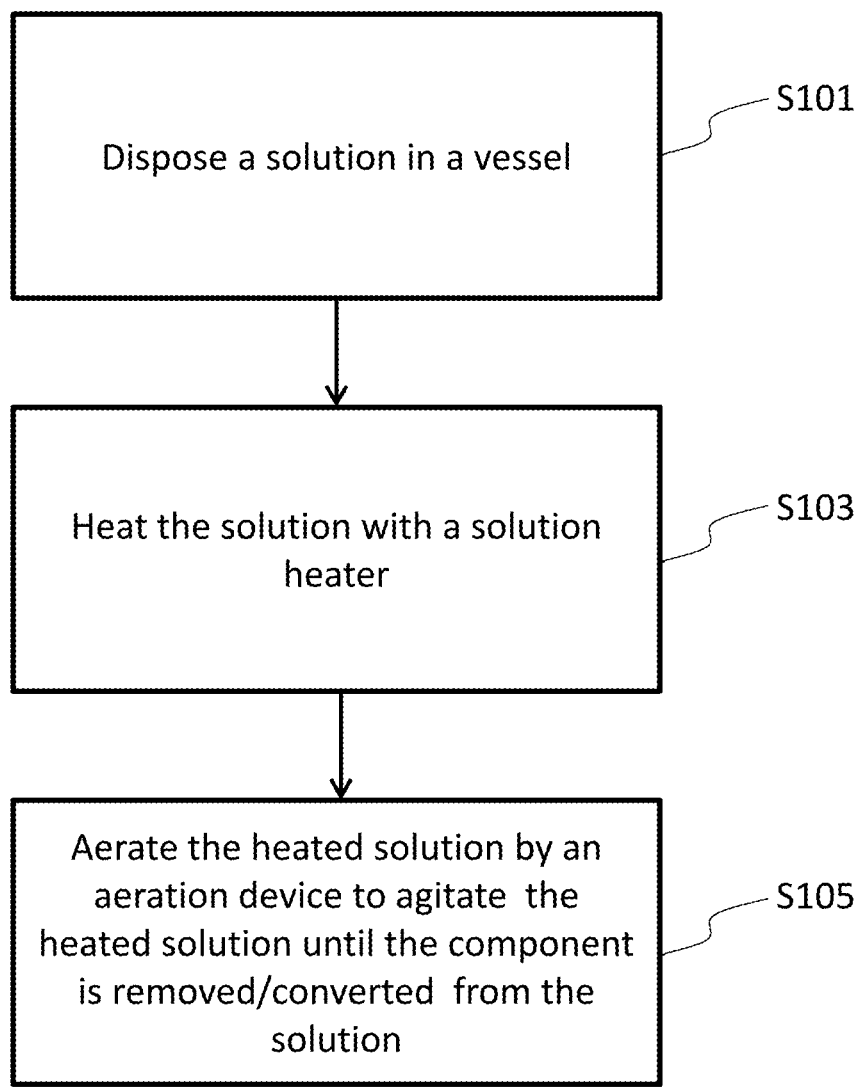
FIG. 7 is a flow chart of a method for removing a component from a solution according to an embodiment of the present disclosure.

Referring to FIG. 7, the step S205 of removing/converting the component from the solution includes the following steps. First step is to dispose the solution into a vessel S101, wherein the solution contains the component that needs to be converted/removed. In step S103, the solution is heated with a solution heater. The solution heater keeps the solution at a temperature that allows the solution to remain in liquid state so as for aeration to occur in step S105. Step S105 is where the heated solution is aerated by an aeration device and thereby being agitated, and the act of aeration and agitation continues until the component is removed/converted from the solution.

More specifically, the aeration device includes at least one aeration pipe disposed in the vessel, a gas source in fluid connection to the aeration pipe, and a gas heater disposed between the aeration pipe and the gas source. To achieve the aeration in step S105, a gas is provided from the gas source and heated with the gas heater, and then the heated gas is introduced into the heated solution via the aeration pipe.

In addition, an external influence is applied to the heated solution in step S205 to assist in converting/removing the component from the solution. In the first embodiment of the present disclosure, the external influence is to heat the gas to a temperature higher than the heated solution. In the second embodiment of the present disclosure, the external influence is the addition of the oxidizing agent to the heated solution. The oxidizing agent is, for example, ozone. In the third embodiment of the present disclosure, the external influence is to irradiate the heated solution by a radiation device, wherein the radiation device includes an electromagnetic spectrum source and a filter. When the electromagnetic spectrum source is an IR lamp, preferably with a wide spectrum radiation range, the filter limits a radiation exposure and narrows it to a desired spectrum preferably in a range of 2-25 micrometers.

In view of the above, the present disclosure provides an apparatus and method for removing a component from a solution by conversion, wherein external influence and aeration are utilized to achieve component conversion/removal in low heat. In comparison to the conventional component removal apparatus and methods, the apparatus and method of the present disclosure carries out the removal of component in the solution with minimal heat on both the starting material and the constituents and the volatile components can be reintroduced into the solution for maintaining the original compositions of the solution but less the removed component.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

What is claimed is:

1. An apparatus for converting and thus removing a component from a full spectrum *cannabis* oil, the apparatus comprising:
    a vessel for containing the full spectrum *cannabis* oil;
    a solution heater connected to or in contact with the vessel for heating the full spectrum *cannabis* oil; and
    an aeration device connected to the vessel for providing aeration to the heated full spectrum *cannabis* oil;
    wherein the heated full spectrum *cannabis* oil is agitated by the aeration and the component is thereby converted and thus removed therefrom;
    wherein the aeration device comprises: (1) at least one aeration pipe disposed in the vessel; (2) a gas source in fluid connection with the at least one aeration pipe for providing a gas; (3) a gas heater disposed between the gas source and the at least one aeration pipe for heating the gas before introducing the gas into the at least one aeration pipe; and (4) a temperature sensor disposed between the gas heater and the at least one aeration pipe for controlling a temperature of the heated gas; and
    wherein the component is tetrahydrocannabinol (THC).

2. The apparatus of claim 1, wherein the gas source is a gas tank or a gas generator.

3. The apparatus of claim 1, wherein the gas is a compressed gas, a combined gas mixture of non-naturally occurring gas, oxygen, nitrogen, air, argon, or any combination thereof.

4. The apparatus of claim 1, further comprising a lid disposed over the vessel.

5. The apparatus of claim 1, wherein the aeration of the heated full spectrum *cannabis* oil comprises an addition of an oxidizing agent.

6. The apparatus of claim 5, wherein the oxidizing agent is ozone and the apparatus further comprises an ozone generator connected to the aeration device.

7. The apparatus of claim 1, further comprising a radiation device disposed at a top of the vessel for irradiating the heated full spectrum *cannabis* oil, wherein the radiation device comprises an electromagnetic spectrum source.

8. The apparatus of claim 7, wherein the electromagnetic spectrum source is an IR lamp and the radiation device further comprises a filter disposed between the electromagnetic spectrum source and the heated full spectrum *cannabis* oil for limiting a radiation exposure to a desired spectrum.

9. The apparatus of claim 8, wherein the IR lamp is an IR lamp with a spectrum radiation range of 2-25 micrometers.

10. The apparatus of claim 7, wherein the electromagnetic spectrum source is a coil or an antenna focusing EMI energy to the heated solution.

11. The apparatus of claim 1, wherein a temperature of the heated gas is higher than a temperature of the heated full spectrum *cannabis* oil.

12. The apparatus of claim 1, wherein the THC is converted by degradation.

13. A method for converting and thus removing a component from a full spectrum *cannabis* oil, the method comprising:
    disposing the full spectrum *cannabis* oil in a vessel;
    heating the full spectrum *cannabis* oil with a solution heater; and
    aerating the heated full spectrum *cannabis* oil by an aeration device to agitate the heated full spectrum *cannabis* oil, and thereby the component is converted and thus removed therefrom;
    wherein the component is tetrahydrocannabinol (THC).

14. The method of claim 13, wherein the aeration device comprises at least one aeration pipe disposed in the vessel, a gas source in fluid connection with the at least one aeration pipe, and a gas heater disposed between the at least one aeration pipe and the gas source, and the step of aerating the heated solution comprises:
- providing a gas from the gas source;
- heating the gas with the gas heater to a temperature higher than the heated full spectrum *cannabis* oil; and
- introducing the heated gas into the heated full spectrum *cannabis* oil via the at least one aeration pipe.

15. The method of claim 14, further comprising:
adding an oxidizing agent to the heated gas.

16. The method of claim 13, further comprising:
irradiating the heated full spectrum *cannabis* oil by a radiation device.

17. The method of claim 15, further comprising irradiating the heated full spectrum *cannabis* oil by a radiation device, wherein the oxidizing agent is ozone, and the radiation device comprises an electromagnetic spectrum source disposed at a top of the vessel and a filter disposed between the electromagnetic spectrum source and the heated full spectrum *cannabis* oil, wherein the electromagnetic spectrum source is an IR lamp and the filter limits a radiation exposure to a desired spectrum.

18. The method of claim 17, wherein the IR lamp is an IR lamp with a spectrum radiation range of 2-25 micrometers.

19. The method of claim 13, wherein the full spectrum *cannabis* oil is a processed full spectrum *cannabis* oil, further comprising the preliminary steps of:
- performing an HPLC/GC chromatography analysis on a first full spectrum *cannabis* oil;
- removing volatile compounds from the first full spectrum *cannabis* oil to obtain the processed full spectrum *cannabis* oil; and
- configuring the vessel, the solution heater, and the aeration device based on results of previous implementation of a method of claim 13;
- wherein the processed full spectrum *cannabis* oil is used as a first starting material for the subsequent steps of the method.

20. The method of claim 19, wherein after the component is converted and thus removed from the processed full spectrum *cannabis* oil, a second HPLC chromatography analysis is performed and if a result of the analysis meets a pre-determined standard, the volatile compounds are re-introduced to the processed full spectrum *cannabis* oil, and if the result does not meet the pre-determined standard, said subsequent steps are repeated wherein the processed full spectrum *cannabis* oil having the component being removed therefrom serves as a second starting material in the repeated process.

21. The method of claim 19, wherein the volatile compounds are terpenes.

22. The method of claim 13, wherein the THC is converted by degradation.

23. A *cannabis* oil processing system comprising:
- a full spectrum *cannabis* oil;
- a vessel for containing the full spectrum *cannabis* oil;
- a solution heater connected to or in contact with the vessel for heating the full spectrum *cannabis* oil; and
- an aeration device connected to the vessel for providing aeration to the full spectrum *cannabis* oil;
- wherein the heated full spectrum *cannabis* oil is agitated by the aeration and a component is thereby converted and thus removed therefrom; and
- wherein the component is tetrahydrocannabinol (THC).

24. The *cannabis* oil processing system of claim 23, wherein the aeration device comprises: (1) at least one aeration pipe disposed in the vessel; (2) a gas source in fluid connection with the at least one aeration pipe for providing a gas; (3) a gas heater disposed between the gas source and the at least one aeration pipe for heating the gas before introducing the gas into the at least one aeration pipe; and (4) a temperature sensor disposed between the gas heater and the at least one aeration pipe for controlling a temperature of the heated gas.

25. The *cannabis* oil processing system of claim 23, further comprising a radiation device disposed at a top of the vessel for irradiating the heated full spectrum *cannabis* oil, wherein the radiation device comprises an electromagnetic spectrum source.

26. A method for converting and thus removing tetrahydrocannabinol (THC) from a full spectrum *cannabis* oil, the method comprising:
- heating the full spectrum *cannabis* oil to a temperature ranging from 40° C. to 90° C.; and
- aerating the heated full spectrum *cannabis* oil with a gas preheated to a temperature ranging from 145° C. to 200° C. to agitate the heated full spectrum *cannabis* oil, thereby converting and thus removing THC therefrom.

27. The method of claim 26, further comprising irradiating the heated full spectrum *cannabis* oil by a radiation device to facilitate conversion of THC.

28. The method of claim 26, wherein the THC is converted by degradation.

* * * * *